United States Patent
Damme et al.

[11] Patent Number: 6,160,147
[45] Date of Patent: Dec. 12, 2000

[54] SILYLATING AGENT

[75] Inventors: Eric Damme, Marche lez Ecaussinnes; Jean de la Cro Habimana, Braine le Comte, both of Belgium; Fabrice Lebecq, Midland, Mich.; David Wilson, Penarth, United Kingdom

[73] Assignee: Dow Corning Limited, Barry, United Kingdom

[21] Appl. No.: 09/458,253

[22] Filed: Dec. 9, 1999

[30] Foreign Application Priority Data

Dec. 9, 1998 [GB] United Kingdom .................... 9827088

[51] Int. Cl.[7] ................................. C07F 7/08; C07F 7/10
[52] U.S. Cl. .......................... 556/411; 556/400; 556/450; 556/451
[58] Field of Search ..................... 556/411, 400, 556/450, 451

[56] References Cited

U.S. PATENT DOCUMENTS 4,059,559 11/1977 Burkhardt et al. .................... 260/448.2
5,021,600 6/1991 Cardinali et al. ........................ 556/411

FOREIGN PATENT DOCUMENTS 2252975 8/1992 United Kingdom .

*Primary Examiner*—Paul F. Shaver
*Attorney, Agent, or Firm*—Jennifer S. Warren

[57] ABSTRACT

A compound of formula (I) is disclosed for use as a silylating agent:

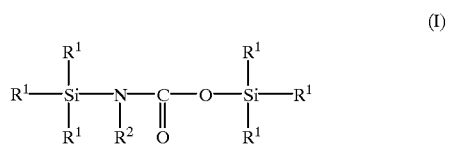

wherein each $R^1$ is independently a hydrogen atom, an alkyl group or an alkenyl group with at least one $R^1$ being a hydrogen atom or alkenyl group, and $R^2$ is a hydrogen atom or an alkyl group. Also disclosed is a method of making the compound, and a method of using the compound as a silylating agent.

7 Claims, No Drawings

SILYLATING AGENT

FIELD OF THE INVENTION

The present invention relates to silylating agents for adding functional groups to materials containing silanol groups, for example silanol terminated siloxanes and silica. The present invention also relates to a method for making said compounds, and a method for adding functional groups to materials containing silanol groups using said compounds as silylating agents.

BACKGROUND OF THE INVENTION

High molecular weight organo-functional endblocked polysiloxanes may be produced by condensation polymerisation of relatively low molecular weight linear silanol functional organosiloxanes in the presence of a low molecular weight organo-functional endblocked organosiloxane and a suitable catalyst. For example, GB Patent 2,252,975 describes a method for making organopolysiloxanes from organosiloxanes using a phosphonitrile halide catalyst. A problem associated with such condensation polymerisation processes is the amount of residual silanol functional polyorganosiloxane remaining in the reaction mixture after completion of the polymerisation reaction, which amount tends to increase as a function of the viscosity of the desired product polyorganosiloxane. There has thus been a need for an effective silylating agent which can react with such residual silanol to afford the desired functionality, and which can also react with other silanol groups, such as those on the surface of silica particles and other materials for use as filler in, for example, silicone rubber, and silanol on the surface of substrates such as glass. Silylacetamide is an effective silylating agent but generates acetamide, a solid by-product which is difficult to remove from the reaction mixture. Cyclic trisilazane is another effective silylating agent but is also a chain extender which leads to broadening of molecular weight distribution. U.S. Pat. No. 4,059,559 discloses the use of disilazanes as silylating agents.

SUMMARY OF THE INVENTION

One aspect of this invention is a compound of formula (I) for use as a silylating agent:

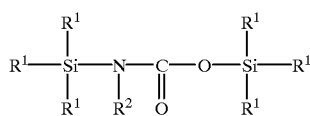
(I)

wherein each $R^1$ is independently selected from the group consisting of a hydrogen atom, an alkyl group and an alkenyl group with at least one $R^1$ being selected from the group consisting of a hydrogen atom and an alkenyl group, and $R^2$ is selected from the group consisting of a hydrogen atom and an alkyl group.

A second aspect of this invention is a method for making a compound of formula(I) comprising a first step of reacting a primary amine with carbon dioxide in the presence of a tertiary amine to form a trialkylammonium salt of an N-alkylcarbamate, and a second step of reacting a silane having the formula $R^1{}_3SiX$ with the trialkylammonium salt to form the compound of formula(I).

A third aspect of the present invention is the use of components of formula (I) to silylate materials having silanol groups. The present inventors have found bis-dimethylsilyl-carbamates to be effective silylating agents for adding functional groups to silanol functional organopolysiloxanes, silica, and other inorganic fillers and substrates, providing a fast reaction with silanol groups and leaving volatile by-products.

DETAILD DESCRIPTION OF THE INVENTION

According to the present invention in a first aspect there is provided a compound of formula (I) for use as a silylating agent:

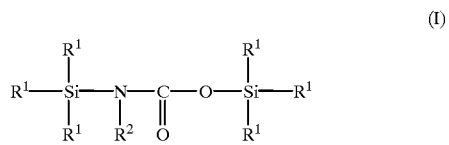
(I)

wherein each $R^1$ is independently a hydrogen atom, an alkyl group or an alkenyl group with at least one $R^1$ being a hydrogen atom or alkenyl group, and $R^2$ is a hydrogen atom or an alkyl group.

Preferably each $R^1$ in formula (I) above is independently a methyl group, a hydrogen atom or an alkenyl group.

As an alkenyl group, $R^1$ may have from 2 to 6 carbon atoms, i.e. vinyl, propenyl, butenyl, pentenyl and hexenyl, and is preferably vinyl or hexenyl. $R^1$ is most preferably a hydrogen atom, a vinyl or a hexenyl group.

As an alkyl group, $R^1$ may have from 1 to 6 carbon atoms, i.e. methyl, ethyl, propyl, butyl, pentyl and hexyl, and is preferably methyl.

As an alkyl group, $R^2$ may be any of the groups mentioned above in this regard for $R^1$, and is preferably a propyl group.

The compound of the present invention is preferably N-Pr,bis(vinyldimethylsilyl)carbamate, N-Pr,bis(hydrogendimethylsilyl)carbamate, or N-Pr,bis(hexenyldimethylsilyl)-carbamate.

According to the present invention there is provided in a second aspect a method for making a compound of formula (I)

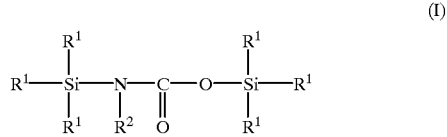
(I)

which method comprises a first step of reacting a primary amine with carbon dioxide in the presence of a tertiary amine to form a trialkylammonium salt of an N-alkylcarbamate, and a second step of reacting a silane having the formula $R^1{}_3SiX$ with the trialkylammonium salt to form the compound of formula I, wherein each $R^1$ is independently a hydrogen atom, an alkyl group or an alkenyl group with at least one $R^1$ being a hydrogen atom or alkenyl group, $R^2$ is an alkyl group and X is a leaving group.

The method of the second aspect of the present invention may thus be represented by the reaction scheme:

$$R^2NH_2 + CO_2 + 2R^3{}_3N \rightarrow R^2NHCO_2{}^- R^3{}_3NH^+ \quad (1)$$

$$R^2NHCO_2{}^- R^3{}_3N^+ + 2R^1{}_3SiX \rightarrow R^1{}_3SiNR^2CO_2SiR^1{}_3 + 2R^3{}_3N.HCl \quad (2)$$

wherein $R^1$, $R^2$ and X are as defined above and $R^3$ is an alkyl group, for example methyl or ethyl. X may be a halogen atom (e.g. chlorine, bromine, iodine). $R^3$ is preferably ethyl and X is preferably a chlorine atom.

In step (1) of the method of the second aspect of the present invention, a primary amine is reacted with $CO_2$ in the presence of a tertiary amine to trap the acid formed during the reaction and to form a trialkylammonium salt of an N-alkylcarbamate. The reaction is exothermic and hence cooling of the reaction mixture may be required, for example to 0° C. or below (e.g. to a temperature between −20 and −30° C.). In step (2), reaction of the silane with the trialkylammonium salt is also exothermic and the silane may need to be added gradually, for example dropwise, with cooling of the reaction mixture. The specific reaction conditions to be employed will of course depend upon the particular compound being made. Where the desired end-product is an asymmetric carbamate, for example hydrogendimethylsilyl-vinyldimethylsilylcarbamate, then different silanes are used sequentially in different steps.

According to the present invention in a third aspect there is provided a method for silylating a material having a silanol group which method comprises reacting the material having the silanol group with a compound of formula (I):

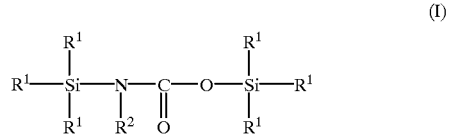

wherein each $R^1$ is independently a hydrogen atom, an alkyl group or an alkenyl group with at least one $R^1$ being a hydrogen atom or alkenyl group, and $R^2$ is a hydrogen atom or an alkyl group.

The reaction of the third aspect of the present invention may thus be represented by the reaction scheme:

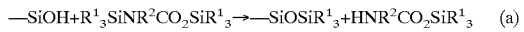

wherein $R^1$ and $R^2$ are as defined above in relation to formula (I).

The compounds of the first aspect of the present invention are thus useful as silylating agents to reduce the amount of silanol groups and optimize the functionality of an polyorganosiloxane, silicone resin, silica, other inorganic filler or substrate by using the method of the third aspect of the present invention.

In the method of the third aspect of the present invention, the compounds of the first aspect can merely be added to the silanol containing polyorganosiloxane, silica or other inorganic filler and mixed at room temperature. For substrates such as a pane of glass the compounds of the first aspect may simply be coated onto the substrate.

Materials silylated by the method of the third aspect of the present invention may be end-products per se, or may be further reacted to form further products. For example, an polyorganosiloxane having vinyl functionality may be further reacted with an organosilicon compound having Si—H groups in the presence of a noble metal catalyst by a hydrosilylation reaction to cross-link the polyorganosiloxane and thus form a more highly structured material.

The present invention will now be illustrated by way of example.

EXAMPLE 1
synthesis of dimethylsilylcarbamates
a) N-Pr,bis(hydrogendimethylsilyl)carbamate 100 ml of dry dichloromethane, 6 g of isopropylamine and 10.1 g of triethylamine were mixed in a flask and cooled to between −20 and −30° C. Dry $CO_2$ was then bubbled through the solution until saturation. The $CO_2$ inlet was then replaced by a dropping funnel containing 20.1 g of hydrogendimethyl-chlorosilane which silane was slowly added to the mixture with mixing whilst maintaining the temperature of the mixture below 20° C. The mixture was then allowed to warm to room temperature, and dichloromethane was removed by distillation. A triethylammonium salt was removed from the reaction mixture by selective precipitation using n-pentane. After filtration, the solution was concentrated under vacuum to give a transparent yellow liquid. $^{29}Si$ NMR and FTIR studies confirmed the product as N-Pr, bis(hydrogendimethylsilyl)-carbamate.

b) N-Pr, bis(vinyldimethylsilyl)carbamate

N-Pr,bis(vinyldimethylsilyl)carbamate was prepared using the method described in a) directly above with the exception that vinyldimethylchlorosilane was used as the silane.

c) N-Pr,bis(hexenyldimethylsilyl)carbamate

N-Pr,bis(hexenyldimethylsilyl)carbamate was prepared he method described in a) directly above was followed to with the exception that hexenyldimethylchlorosilane was used as the silane.

EXAMPLE 2
endcapping of silanol-endblocked polydimethyl-siloxane

A silanol-endblocked polydimethylsiloxane (PDMS) having a degree of polymerisation of 100 was treated with N-Pr,bis-(hydrogendimethylsilyl)carbamate and analysed by NMR. The results are shown in Table 1:

TABLE 1

|  | PDMS (g) | Carbamate (g) | Silanol (ppm) | Silanol (mol) |
|---|---|---|---|---|
| Sample 1 | 5 | 0 | 9087 | $5.34 \times 10^{-4}$ |
| Sample 2 | 5 | 0.15 | 7805 | $4.59 \times 10^{-4}$ |
| Sample 3 | 5 | 0.5 | <50 | — |

Upon addition of the carbamate the PDMS became hazy and a strong amine smell developed due to the release of isopropylamine. As the amount of added carbamate was increased the silanol signal decreased until at 10% wt. carbamate it disappeared altogether.

EXAMPLE 3
polymer functionalization and catalyst neutralisation 2000 g of silanol end-blocked PDMS of approximately 70 $mm^2/s$ viscosity was polymerised in the presence of 40 ppm of phosphonitrile chloride antimonate catalyst at 25° C. and a pressure of 10 kPa. N-r,bis(hydrogendimethylsilyl) carbamate was injected into the reaction mixture to functionalize the polymer and neutralise the catalyst when the desired polymer viscosity was reached. The results are shown in Table 2 below. "BDSC" means N-Pr,bis (hydrogendimethylsilyl)-carbamate:

TABLE 2

| Exp. 1 5.9 g BDSC | | Exp. 2 3.15 g BDSC | | Exp. 3 1.98 g BDSC | | Exp. 4 1.02 g BDSC | |
|---|---|---|---|---|---|---|---|
| Time (s) | Torque (A) | Time (s) | Torque (A) | Time (s) | Torque (A) | Time (s) | Torque (A) |
| 0 | 1.41 | 0 | 1.39 | 0 | 1.41 | 0 | 1.39 |
| 60 | 1.41 | 60 | 1.39 | 60 | 1.41 | 180 | 1.39 |
| 360 | 1.41 | 360 | 1.39 | 180 | 1.41 | 720 | 1.40 |
| 720 | 1.41 | 720 | 1.40 | 360 | 1.42 | 780 | 1.41 |

TABLE 2-continued

| | Exp. 1 5.9 g BDSC | | Exp. 2 3.15 g BDSC | | Exp. 3 1.98 g BDSC | | Exp. 4 1.02 g BDSC | |
|---|---|---|---|---|---|---|---|---|
| Time (s) | Torque (A) | Time (s) | Torque (A) | Time (s) | Torque (A) | Time (s) | Torque (A) |
| 900 | 1.41 | 900 | 1.43 | 570 | 1.43 | 810 | 1.43 |
| 1200 | 1.42 | 930 | 1.45 | 660 | 1.45 | 840 | 1.46 |
| 1260 | 1.46 | 960 | 1.47 | 690 | 1.47 | 870 | 1.49 |
| 1290 | 1.48 | 990 | 1.54 | 720 | 1.52 | 900 | 1.55 |
| 1320 | 1.52 | 1020 | 1.66 | 750 | 1.60 | 930 | 1.62 |
| 1410 | 1.83 | 1050 | 1.95 | 780 | 1.75 | 960 | 1.68 |
| | | 1080 | 1.99 | 810 | 1.98 | 990 | 1.88 |
| | | | | | | 1020 | 1.95 |
| SiH ppm | 9.1 | | 9.9 | | 5.5 | | <3 |
| SiOH ppm | 403 | | 342 | | 366 | | 304 |
| Viscosity mm$^2$/s | 36k | | 63.4k | | 57.8k | | 51.5k |

EXAMPLE 4
polymer functionalization and characterization oxy index

Hydroxy index method is used to determine the amount of residual silanol remaining in a siloxane polymer. Silanol containing polyorganosiloxane is treated with excess polymethylhydrogensiloxane in the presence of a tin catalyst. Residual silanol groups react with the polymethylhydrogensiloxane to form a resin. The viscosity of the mixture increases in proportion to the amount of residual silanol present. The lower the hydroxy index the higher the level of residual silanol. The hydroxy index method was thus used to determine the levels of residual silanol in Si—OH end-blocked PDMS and Si—H terminated PDMS which had been treated with different amounts of BDSC. The results are shown in Tables 3 and 4 below:

TABLE 3

| Sample | PDMS (g) | BDSC (g) | Temp (° C.) | Time (s) | Viscosity (mm$^2$/s) | Hydroxy index |
|---|---|---|---|---|---|---|
| 1 | 140 | — | — | — | 12300 | Gel |
| 2 | 140 | 0.21 | 60 | 900 | 12300 | Gel |
| 3 | 140 | 0.34 | 60 | 900 | 12300 | 0.47 |
| 4 | 140 | 0.52 | 60 | 900 | 12300 | 0.97 |

TABLE 4

| Sample | Si—H PDMS (g) | BDSC (g) | Temp (° C.) | Time (s) | Viscosity (mm$^2$/s) | Hydroxy index |
|---|---|---|---|---|---|---|
| 1 | 140 | — | — | — | 13,700 | 0.12 |
| 2 | 140 | 0.15 | 60 | 900 | 13,700 | 0.25 |
| 3 | 140 | 0.30 | 60 | 900 | 12,300 | 0.76 |
| Computed | 140 | 0.41 | | | 12,300 | 1.0 |

Tables 3 and 4 show how the hydroxy index increases as the amount of added BDSC increases.

EXAMPLE 5
BDSC treatment of silica 150 g of silica was placed in a 2 liter round bottomed flask having a central stirrer. 34.7 g BDSC was introduced into the flask slowly with stirring at room temperature under a nitrogen blanket.

The extent of surface modification of the silica was determined by diffuse reflectance infrared fourier transform spectroscopy (DRIFTS). The DRIFTS spectrum indicated that the silica had been substantially silylated by the BDSC—silanol vibrations at 3740 cm$^{-1}$ had been substantially reduced and a strong peak attributed to Si—H vibrations had appeared at 2140 cm$^{-1}$.

The hydrophobicity of the silica was determined by contact angle measurements with water. The silica was found to be highly hydrophobic with a contact angle of 126+/−3 degrees.

That which is claimed is:

1. A compound of formula (I) for use as a silylating agent:

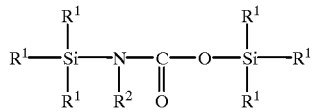

(I)

wherein each $R^1$ is independently selected from the group consisting of a hydrogen atom, an alkyl group and an alkenyl group with at least one $R^1$ being selected from the group consisting of a hydrogen atom and an alkenyl group, and $R^2$ is selected from the group consisting of a hydrogen atom and an alkyl group.

2. A compound according to claim 1 wherein each $R^1$ is independently selected from the group consisting of a methyl group, a hydrogen atom and a vinyl group.

3. A compound according to claim 2 which is selected from the group consisting of N-Pr,bis(vinyldimethylsilyl) carbamate, N-Pr,bis(hydrogen-dimethylsilyl)carbamate, and N-Pr,bis(hexenyldimethylsilyl)-carbamate.

4. A method for making a compound of formula (I):

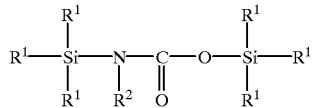

(I)

comprising a first step of reacting a primary amine with carbon dioxide in the presence of a tertiary amine to form a trialkylammonium salt of an N-alkylcarbamate, and a second step of reacting a silane having the formula $R^1_3SiX$ with the trialkylammonium salt to form the compound of formula I, wherein each $R^1$ is independently selected from the group consisting of a hydrogen atom, an alkyl group and an alkenyl group with at least one $R^1$ being selected from the group consisting of a hydrogen atom and an alkenyl group, $R^2$ is an alkyl group and X is a leaving group.

5. A method for silylating a material having a silanol group comprising reacting the material having the silanol group with a compound of formula (I):

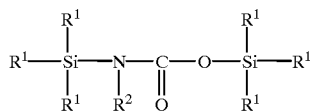

(I)

wherein each $R^1$ is independently selected from the group consisting of a hydrogen atom, an alkyl group and an alkenyl group with at least one $R^1$ being selected from the group consisting of a hydrogen atom and an alkenyl group, and $R^2$ is selected from the group consisting of a hydrogen atom and an alkyl group.

6. The method of claim 5 where the material having the silanol group is a silanol-endblocked polydimethylsiloxane.

7. The method of claim 5 where the material having the silanol group is silica.

* * * * *